United States Patent
Uber, III et al.

(10) Patent No.: US 6,375,624 B1
(45) Date of Patent: *Apr. 23, 2002

(54) EXTRAVASATION DETECTOR USING MICROWAVE RADIOMETRY

(75) Inventors: Arthur E. Uber, III; David M. Griffiths, both of Pittsburgh, PA (US)

(73) Assignee: Medrad, Inc., Indianola, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/398,658

(22) Filed: Sep. 17, 1999

Related U.S. Application Data

(63) Continuation of application No. 08/663,710, filed on Jun. 14, 1996, now Pat. No. 5,954,668.

(51) Int. Cl.$^7$ .............................................. A61B 5/00

(52) U.S. Cl. .............................. 600/549; 128/DIG. 13; 604/52

(58) Field of Search ........................... 600/549; 73/346; 604/49–50, 52; 374/122, 148; 128/DIG. 12, 13

(56) References Cited

U.S. PATENT DOCUMENTS

| | | | |
|---|---|---|---|
| 3,779,079 A | | 12/1973 | Snook |
| 3,951,136 A | * | 4/1976 | Wall ....................... 128/DIG. 4 |
| 4,010,749 A | | 3/1977 | Shaw |
| 4,378,808 A | | 4/1983 | Lichtenstein |
| 4,575,705 A | * | 3/1986 | Gotcher ....................... 374/208 |
| 4,647,281 A | | 3/1987 | Carr |
| 4,648,869 A | | 3/1987 | Bobo, Jr. |
| 4,653,501 A | | 3/1987 | Cartmell et al. |

(List continued on next page.)

FOREIGN PATENT DOCUMENTS

| | | |
|---|---|---|
| JP | 11-57001 | 3/1999 |
| WO | WO 99/26685 | 6/1999 |

OTHER PUBLICATIONS

Shaeffer, PhD, Early Detection of Extravasation of Radiographic Contrast Media, 141–144, Contrast Media Radiology.

Shaeffeer, PhD, Detection of Extravasation of Antineoplastic Drugs by Microwave Radiometry, Cancer Letters, 31 (1986) 285–291.

MMIC Receiver for Water–Vapor Radiometer, NASA Tech. Briefs, Sep. 1993; 34.

Arkin, Recent Developments in Modeling Heat Transfer in Blood Perfused Tissues, IEEE Transactions on Biomedical Engineering vol. 41, No. 2, Feb. 1994; 97–107.

Harris & Von Maltzahn, Infusion Line Model for the Detection of Infiltration Extravasation and other Fluid Flow Faults, IEEE Transactions on Biomedical Eng. vol. 40, No. 2, Feb. 1993, 154–162.

Montreuil & Nachman, Multiangle Method for Temperature Measurement of Biological Tissues by Mircrowave Radiometry, IEEE Transactions on Microwave Theory and Techniques, vol. 39, No. 7, Jul. 1991, 1235–1238.

*Primary Examiner*—Francis J. Jaworski
(74) *Attorney, Agent, or Firm*—Gretchen Platt Stubenvoll; Gregory L. Bradley

(57) ABSTRACT

A microwave antenna senses the temperature of tissue into which a fluid is to be injected. The fluid is injected by a needle or other vascular entry device connected to a fluid injector by a connector tube. The fluid temperature is measured by a temperature sensor attached to the connector tube. An alarm processor determines whether an extravasation occurs by comparing a temperature discrimination function derived from tissue temperature taken at different times with a calculated threshold value. The threshold value is calculated from the tissue temperature and the fluid temperature. The threshold value is recalculated and updated continuously during the fluid injection.

37 Claims, 16 Drawing Sheets

U.S. PATENT DOCUMENTS

| | | |
|---|---|---|
| 4,816,019 A | 3/1989 | Kamen |
| 4,877,034 A | 10/1989 | Atkins et al. |
| 4,959,050 A | 9/1990 | Bobo, Jr. |
| 4,971,068 A * | 11/1990 | Sahi .......................... 601/116 |
| 5,026,348 A | 6/1991 | Venegas |
| 5,334,141 A | 8/1994 | Carr et al. |
| 5,769,784 A * | 6/1998 | Barrett et al. ............... 600/300 |
| 5,947,910 A | 9/1999 | Zimmet |
| 5,954,668 A | 9/1999 | Uber, III et al. |
| 5,964,703 A | 10/1999 | Goodman et al. |

\* cited by examiner

Ts IS THE TISSUE TEMPERATURE AS MEASURED BY THE RADIOMETER

Tf IS THE FLUID TEMPERATURE

RADIOMETER OUTPUT VS. FLUID TEMPERATURE (t=20)

RADIOMETER OUTPUT VS. FLUID TEMPERATURE (t=0)

EXTRAVASATION DETECTOR USING MICROWAVE RADIOMETRY

CROSS-REFERENCE TO RELATED APPLICATIONS

This application is a continuation of application Ser. No. 08/663,710, filed on Jun. 14, 1996 now U.S. Pat. No. 5,954,668, the contents of which are hereby incorporated by reference.

FIELD OF THE INVENTION

This invention relates generally to the field of medical devices for detecting extravasations in fluid injections. More specifically this invention provides an alarm circuit which compares tissue temperature with thresholds calculated from the fluid and tissue temperatures.

BACKGROUND

It is a well known medical procedure to inject a patient with fluids via needle or catheter devices. The needle may be connected to a fluid injector by a connector tube which transmits fluid to the needle. The connector tube may also draw fluids from a container such as an IV bag. In such fluid injections detecting the presence of extravasations or infiltrations of nonvascular tissue is necessary. Extravasations or infiltrations are detected by measuring temperature changes which trigger an Farm condition upon detection of a predetermined temperature deviation from normal skin temperature.

Present systems for detecting extravasations are useful in IV drug infusion applications where the flow rate is slow enough such that the fluid is at room temperature when it is injected. The present methods thus assume a significant and relatively constant difference between fluid temperature and limb temperature.

However with regard to computed tomography ("CT") contrast injection applications, where the flow rates from the fluid injector are in the range of 0.1 to 10 ml/s, the response time for temperature sensing is a significant consideration. A current extravasation detector employs an antenna and radiometer to measure the temperature of the subcutaneous tissue where fluid is injected. An alarm processor uses an algorithm to determine alarm conditions. The algorithm measures the temperature signal periodically and compares it to a fixed threshold level. The extravasation detector system's alarm processor communicates with the fluid injector so the start of the injector and the fluid flow rate are known by the alarm processor. The processor records the temperature signal at the start of the injection. The alarm processor will signal an alarm if the magnitude of deviation from the initial signal exceeds a predetermined magnitude threshold. The magnitude thresholds are taken from tables stored by the processor. The threshold values are predetermined as a function of flow rate and the values are stored in the tables. The alarm signal allows the processor to shut down the fluid injector to prevent further extravasations.

However additional problems are inherent in temperature sensing in extravasation detection. In CT contrast injections the fluid is usually but not always, warmed to a temperature near body temperature. The fluid in the connector tube and the connector tube itself are usually at room temperature. Normally cold fluid is initially injected, followed by warmer fluid. The cold fluid may cause false positive alarms as a small amount of cold fluid in a blood vessel can cause a signal change identical to that of a larger amount of warmer extravasated fluid. Furthermore using preset thresholds does not account for variations in initial patient limb temperature nor variations in fluid temperature during the injection.

Recent passive patient measurement data indicate that limb temperature varies more than had been previously expected. Fluid at 37 degrees Celsius, which is the nominal body temperature, may be warmer than the limbs of most patients. This difference affects the magnitude thresholds for any extravasation decision criteria. Additionally, several patient-specific factors may be useful in setting thresholds to minimize false alarms (false positives) while being sensitive to true extravasations. However predetermined thresholds cannot take these patient-specific factors into account.

Thus an, extravasation and infiltration detection device is needed which can detect true extravasations in high flow injection situations. Furthermore a detection device is needed which can detect true extravasations despite patient variation and temperature changes.

SUMMARY OF THE INVENTION

The invention includes a system for detecting extravasations in tissue injected with fluid from a fluid injector. A fluid temperature sensor senses the temperature of fluid present in a connector tube which transmits fluid to a patient. The fluid temperature sensor generates a fluid temperature signal in response to the fluid in the connector tube. A tissue temperature sensor senses the temperature of the tissue proximate to the site of the injection and generates a tissue temperature signal in response.

A processor receives the tissue temperature signal and the fluid temperature signal. The processor activates an alarm circuit which declares the occurrence of an extravasation, as a function of the tissue temperature signal and the fluid temperature signal during the fluid injection.

A further embodiment of the fluid temperature sensor is used in conjunction with a fluid needle and a fluid connector tube containing fluid. A connector having an interior sidewall connects the tube to the needle. The fluid temperature sensor has a temperature transducer and a metal insert. The metal insert extends through the connector and the interior sidewall. The Metal insert is adaptable to be in contact with fluid in the connector tube to provide a temperature conductive path, and is coupled to the temperature transducer.

The invention also includes a method of detecting extravasations in tissue injected with fluid from a fluid injector. The temperature of fluid present in a connector tube transmitting fluid to a patient is periodically sensed. A fluid temperature signal is generated in response to the temperature of the fluid. The temperature of tissue proximate the site of injection is periodically measured and a tissue temperature signal is generated. The fluid temperature signal and the tissue temperature signal are received and a fluid temperature and a tissue temperature are derived from the received signals. The fluid and tissue temperatures are stored. The occurrence of an extravasation is declared as a function of the tissue temperature signal and the fluid temperature signal during the fluid injection.

Numerous other aspects and advantages of the present invention will become apparent from the following drawings and detailed description of the invention and its preferred embodiment.

DETAILED DESCRIPTION OF THE INVENTION

Figure 1:
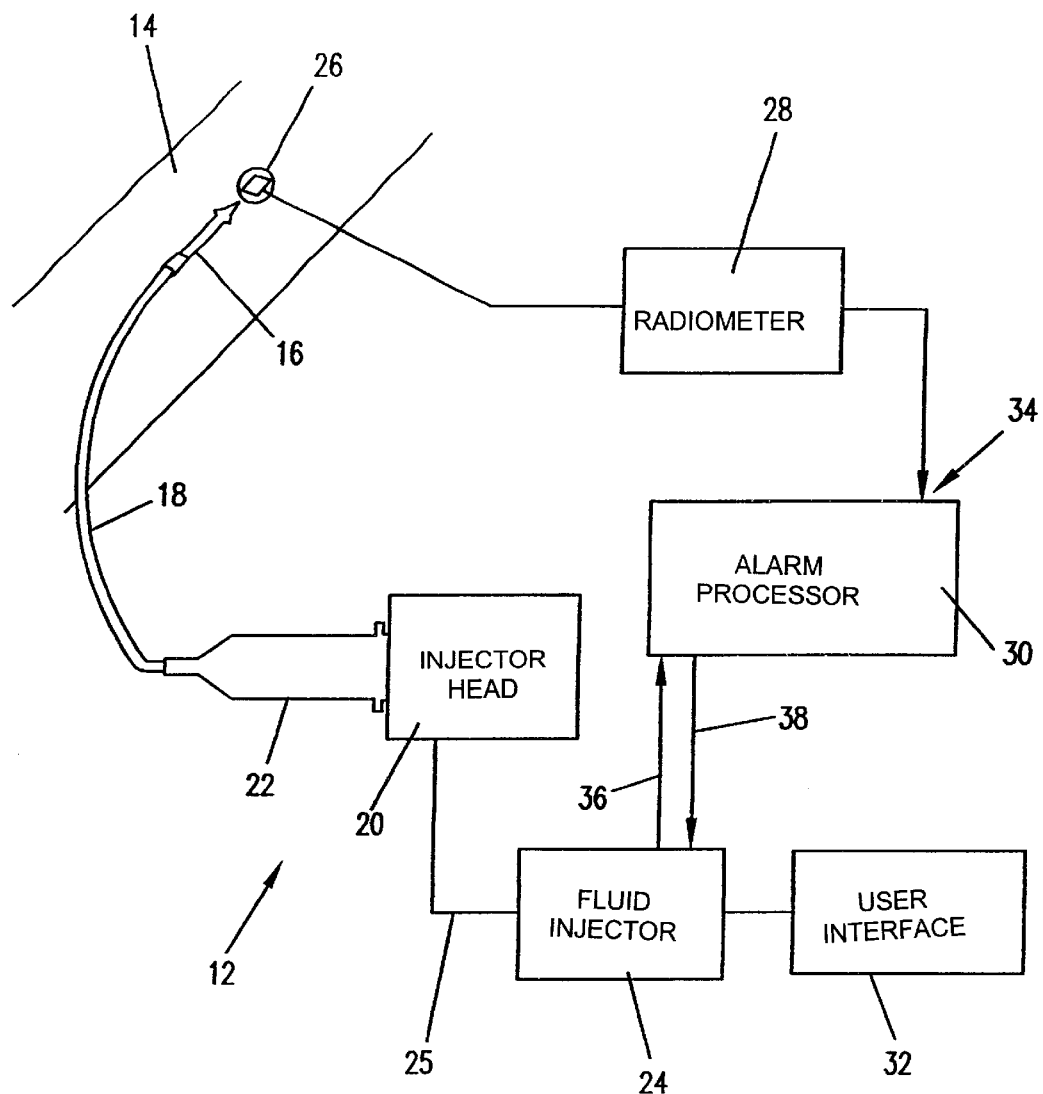
FIG. 1 is a schematic block diagram illustrating a prior art system for sensing extravasations.

FIG. 1 shows a block diagram of a prior art sensing system indicated generally at 12 which is useful for detecting extravasations or infiltrations in fluid injection procedures where the fluid is at or near room temperature and the injection rate is low. The sensing hardware in system 12 employs a strategy of comparing the magnitude of tissue temperature with predetermined fixed thresholds. In the system 12, a needle 16 or other vascular entry device is inserted into a vein in a patient's limb 14. Needle 16 is attached to a connector tube 18, which in turn is connected to a syringe 22. A plunger (not shown) of syringe 22 is slidably displaced within the body of syringe 22 by a piston (not shown) of an injector head 20. Injector head 20 in turn is coupled to a fluid injector 24 by a signal line 25.

The syringe 22 and connector tube 18 are filled with fluid and the needle 16 is placed in the patient's vein. The fluid injector 24 is controlled by a user interface 32 which allows the user to program the injector 24 with the proper flow rate and total volume of fluid to be injected into the patient.

An antenna 26 is placed on the patient's limb 14 near the tip of the needle 16. The antenna 26 receives microwave energy from subcutaneous tissue near the site of injection. A radiometer 28 amplifies the input from the antenna 26 and compares the input to an internal reference. The output of the radiometer 28 is a voltage proportional to the temperature difference between the tissue and the radiometer's internal reference. A typical sensitivity is about 0.3 volts per degree Celsius.

An alarm processor 30 has a radiometer input 34 and a fluid injector in put 36. Radiometer input 34 is connected to the temperature output of the radiometer 28. The radiometer 28 receives power and control functions from a radiometer processor through electrical connections (not shown). Fluid injector input 36 is connected to the injector 24 and carries signals representing the flow rate of the fluid and the start of fluid injection. The alarm processor 30 uses a microprocessor (not shown) to read the temperature signal from the radiometer 28 and the flow rate and the start of fluid injection from the fluid injector 24 to determine the magnitude threshold values. The threshold values are stored in a table and the proper threshold value is selected by the algorithm based on the rate of fluid flow. If the magnitude of the temperature from the radiometer input 34 exceeds the predetermined threshold selected from the stored table an extravasation or infiltration is declared.

In an alternate prior art system the slope of the temperature change per unit time is compared with a second set of alarm thresholds and provides a further basis for declaring that an extravasation has occurred. The alarm processor 30 halts the fluid injector 24 via a control signal through a control output 38. The prior art system 12 is limited in that the use of stored time-invariant thresholds may result in false infiltration and unnecessary interruptions in procedure.

Figure 2:
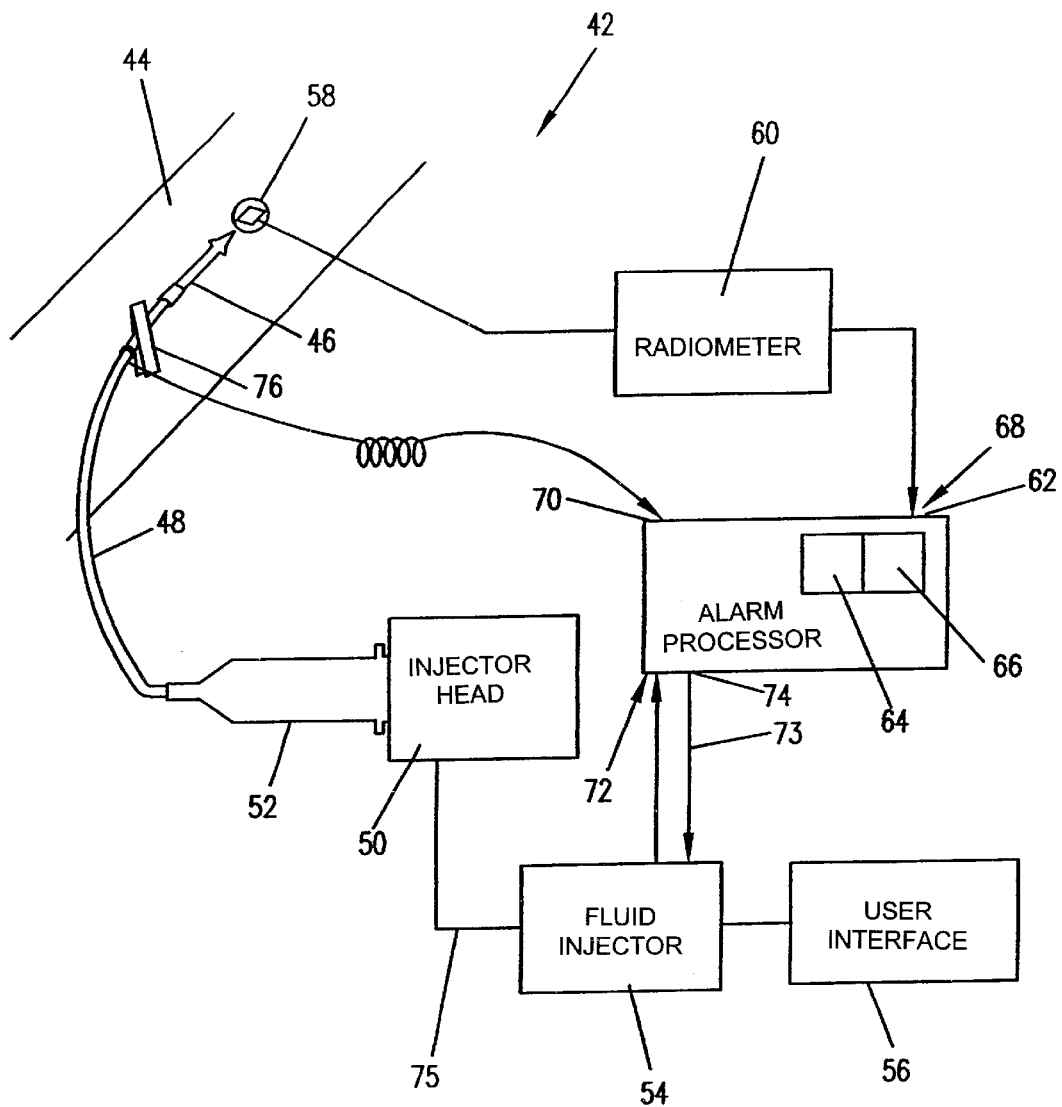
FIG. 2 is a schematic block diagram of an embodiment of the present invention in which a clip-on sensor is used for sensing fluid temperature.

FIG. 2 shows a block diagram of a fluid injector system 42 according to a first embodiment of the present invention. Similar to the prior art system above a needle 46 is inserted in a patient limb 44 to transmit fluid into a blood vessel. The fluid is transmitted to the needle 46 via a connector tube 48 from a syringe 52, which in turn is mounted on an injector head 50. The injector head 50 is controlled by a fluid injector 54 A user may control the start of the fluid flow, the flow rate and the volume of fluid injected through a user interface 56. User interface 56 may also be used to enter patient parameters and select one of a plurality of modes of operation as will be discussed below. The fluid injector 54 senses action and position of the parts of injector head 50, such as piston displacement and motor current and also produces electrical signals indicating that the fluid has begun to flow, the flow rate and the volume of fluid injected.

Extravasations and infiltrations of subcutaneous tissue may be detected during the injection process via an antenna 58 which is placed near the tip of the needle 46. A radiometer 60 is connected to the antenna 58 which amplifies the microwave emissions received by the antenna 58. The radiometer 60 amplifies the signal and produces a voltage output proportional to the difference between subcutaneous tissue temperature and an internal reference. While microwave radiometry is preferred in this embodiment because it can respond more quickly to subsurface tissue temperature variations than a surface temperature sensor can the use of a surface temperature sensor is a viable alternative embodiment, and may be indicated because of decreased costs and increased ease of use.

A clip-on temperature sensor 76 is clipped on the connector tube 48, preferably near the patient limb 44. The clip-on temperature sensor 76 is a temperature measuring transducer such as a thermocouple, or other temperature sensing element such as a thermistor, which is pressed against the outside of connector tube 48 by the clip. The temperature sensor 76 measures the temperature of the outside of the connector tube 48, which is related to the temperature of the fluid injected. There is a time delay due to the thermal mass and low thermal conductivity of the connector tube 48. The output of temperature sensor 76 is connected to fluid temperature input 70 of alarm processor 62. The fluid temperature sensor instead may be incorporated into or mounted on the syringe 52, or at a catheter tip within the catheter, to sense the temperature of the fluid at these alternative points.

An alarm processor 62 has a processor 64 (such as a microprocessor) and a memory 66. The memory 66 stores the extravasation algorithm which will be described below. The memory 66 also stores various input data such as tissue temperature fluid temperature, fluid flow etc. used by the extravasation algorithm. Memory 66 may be Random Access Memory (RAM), magnetic medium or other memory devices. The alarm processor 62 has a tissue temperature input 68, a fluid temperature input 70, and a fluid injector input 72, which are connected to the processor 64. The inputs 68 and 70 receive electrical signals representative of tissue and fluid temperature, respectively. Signals from the fluid injector 54 representing the beginning of fluid flow fluid flow rate and fluid volume are transmitted to the alarm processor 62 via the fluid injector input 72 through a fluid injector input line 71. The processor 64 controls the flow of fluid from syringe 52 via a control output 74 connected to fluid injector 54 by control output line 73.

Figure 3:
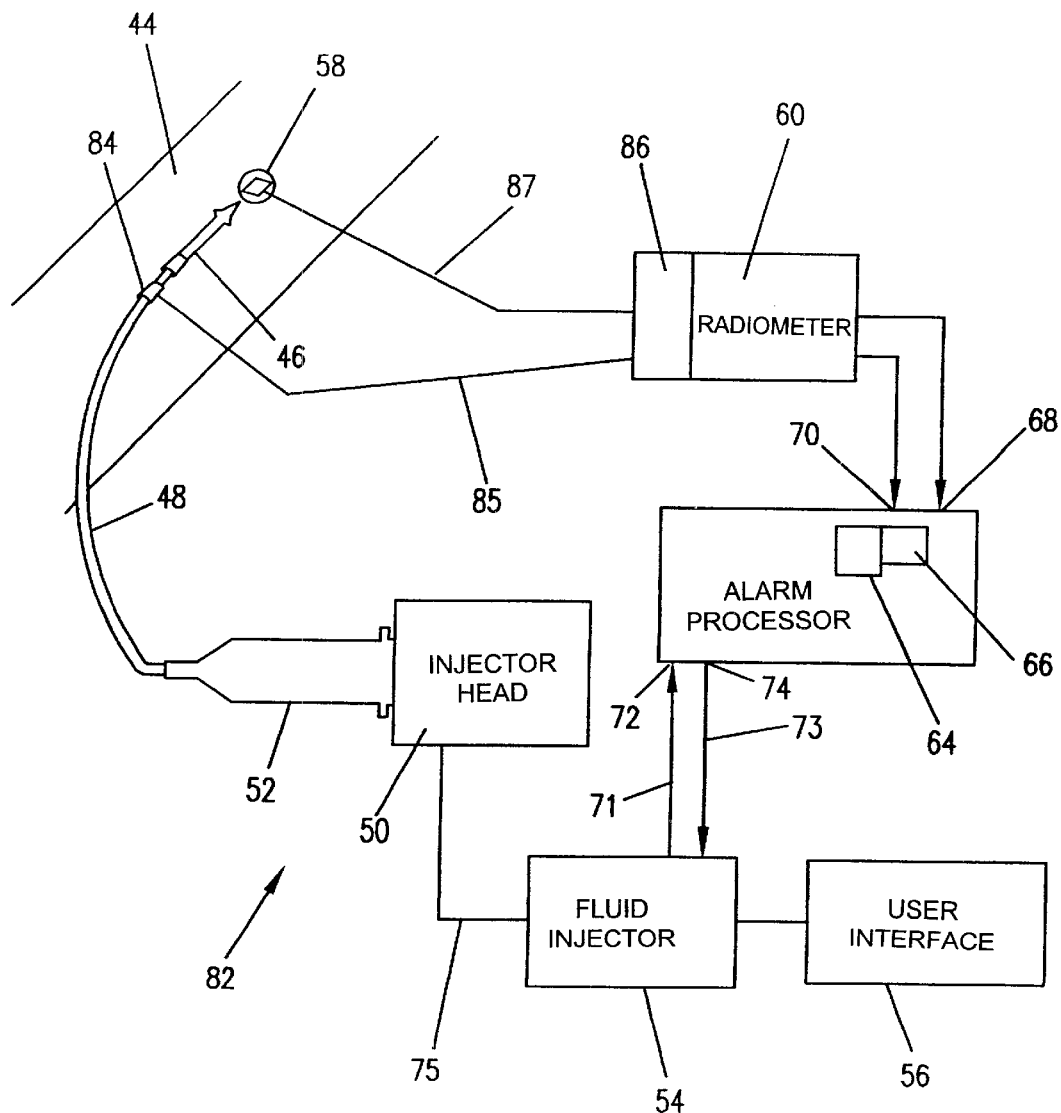
FIG. 3 is a schematic block diagram of an embodiment of the present invention in which a clip-on antenna is used for sensing fluid temperature extravasations.

FIG. 3. is a block diagram of a second embodiment of the present invention indicated generally at 82. Like elements have numbers identical to their counterparts in FIG. 2. A microwave antenna 84 is attached to the connector tube 48 near the patient limb 44 by a connector device such as a clip (not shown). The antenna 84 is connected via a line 85 to a multiplexor 86 in radiometer 60. Multiplexor 86 is also connected to antenna 58 via a signal line 87 and outputs either the signal from antenna 58 representing tissue temperature, or the signal of antenna 84 representing fluid temperature to the remainder of radiometer 60. The radiometer 60 synchronously demodulates the output of the multiplexor 86 into two outputs which are connected to the tissue temperature input 68 and the fluid temperature input 70 of the alarm processor 62. Since its signal is directly related to the temperature of the fluid itself the antenna 84 provides a quick signal response to the fluid temperature in the connector tube 48. In this arrangement, there is no time delay for heat to be conducted through the tubing wall. The multiplexor arrangement may be replaced with a second radiometer (not shown) which would be connected to antenna 84 and input 70.

Figure 4:
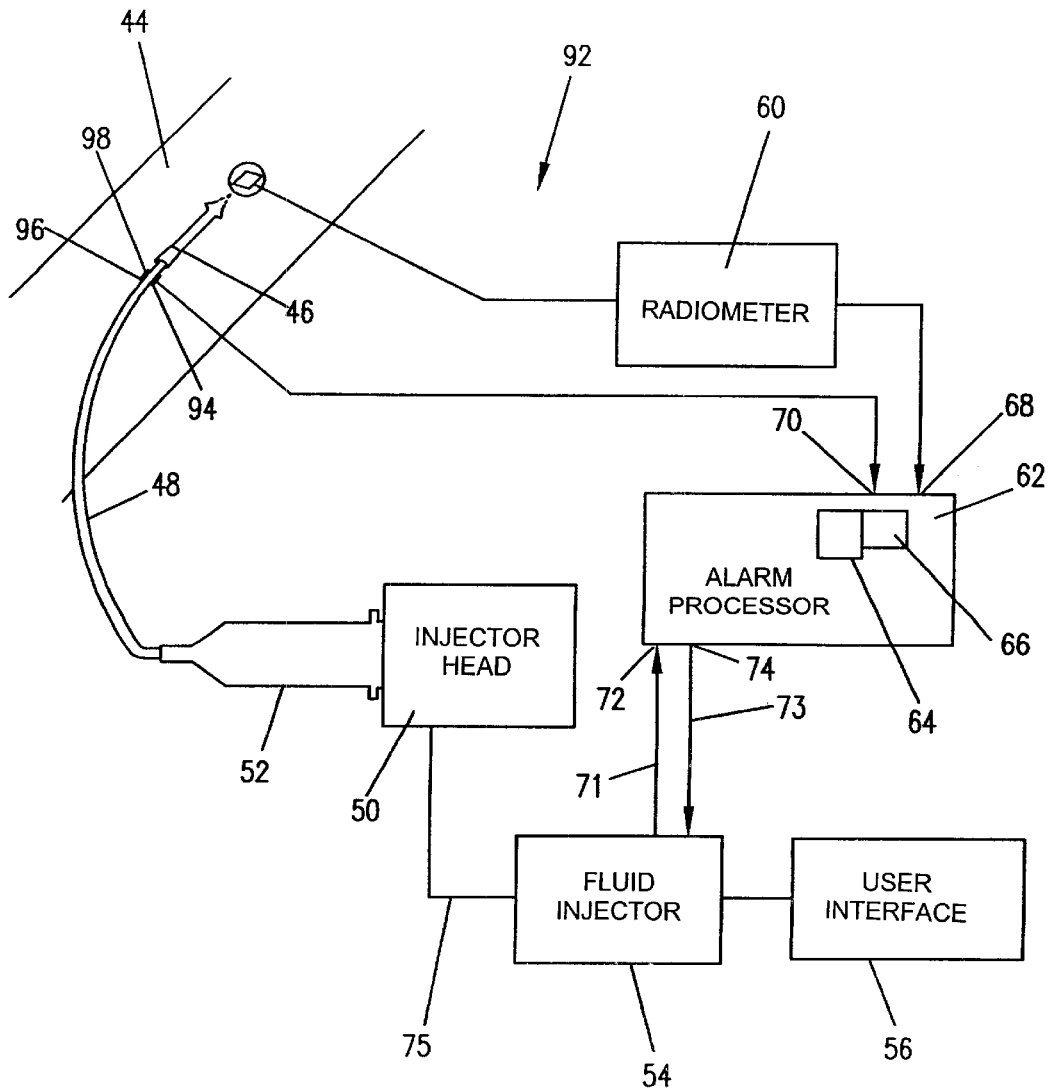
FIG. 4 is a schematic diagram of an embodiment of the present invention in which an in-line sensor is used for sensing fluid temperature.

FIG. 4 is a schematic block diagram of a third embodiment 92 of the present invention where like elements have identical numbers to their counterparts in FIG. 2. An inline temperature sensor 94 is inserted into the connector tube 48 near the patient limb 44. The temperature sensor 94 has a thermistor 96 embedded in a plastic piece 98. The sensor 94 is coated by a thin protective layer of plastic which is welted by the fluid in tube 48. The sensor 94 is preferably disposable and may be replaced for each different injection; it therefore does not have to be made to be as durable as a non-disposable sensor.

Figure 5:
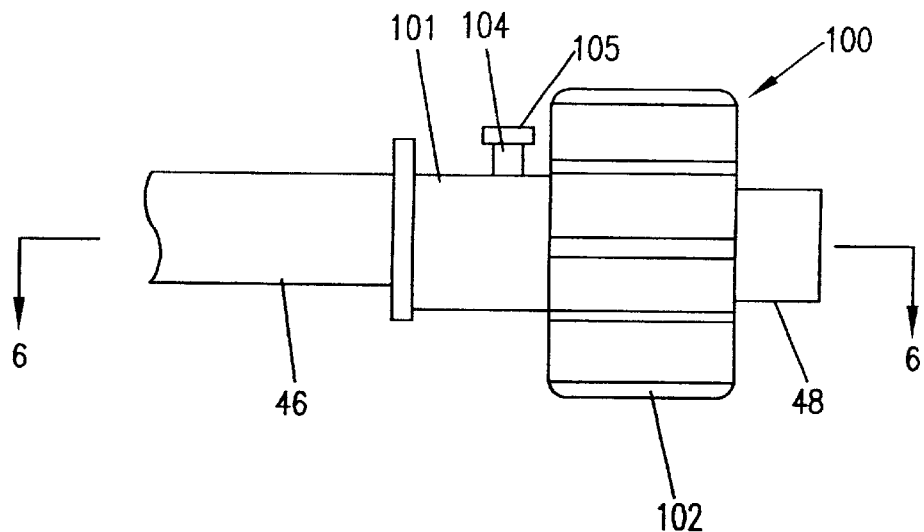
FIG. 5 is a side elevational view of a temperature sensor and fluid connector used in the present invention.
Figure 6:
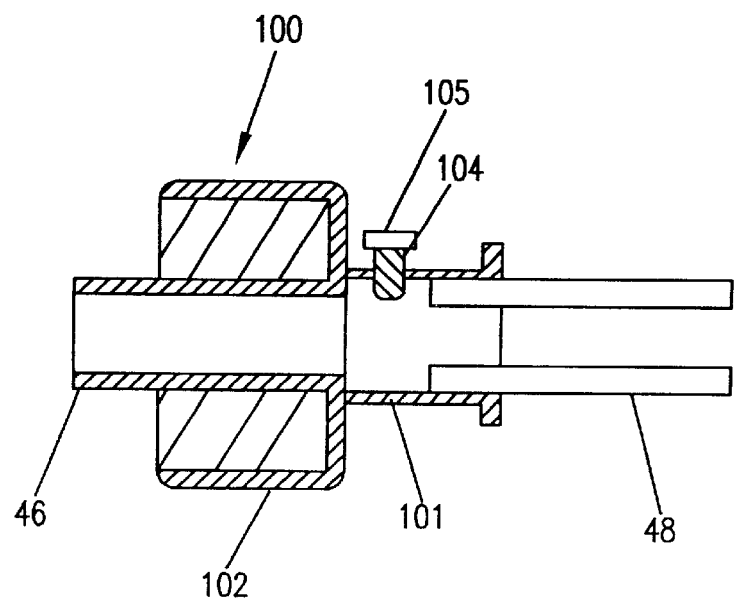
FIG. 6 is an coaxial sectional view taken substantially along line 6—6 of FIG. 5.
Figure 7:
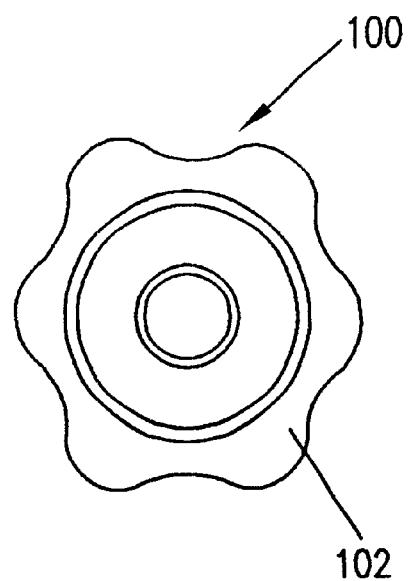
FIG. 7 is a front view of a temperature sensor and fluid connector used in the present invention.
Figure 8:
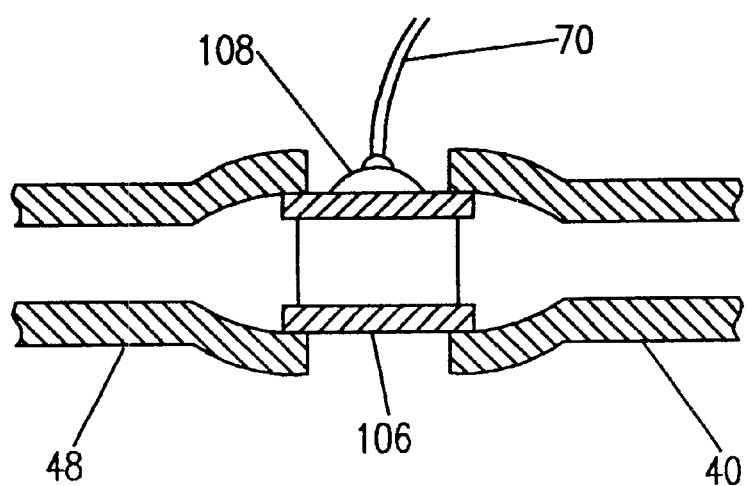
FIG. 8 is an axial sectional view of an alternative temperature sensor according to the invention.

FIGS. 5–7 show an alternate temperature sensor which may replace the temperature sensor 76 in FIG. 2. The connector tube 48 is connected to the needle 46 via a connector indicated generally at 100 which has a threaded collar 102 for receiving needle 46. A thermally conductive insert such as metal piece 104 is inserted into a sidewall 101 of the connector 100. Metal piece 104 serves to quickly conduct heat from the fluid to a clip on temperature transducer 105 which may be a thermistor thermocouple black body radiometer or the like. The metal piece 104 eliminates the time delay of heat conducted through the relatively heat-insulative connector tube 48. An alternative to the metal piece 104 is shown in FIG. 8, which shows the use of a short metal tube section 106 in place of connector 100. Tube 106 is inserted into the length of the connector tube 48 and preferably as close to the patient or possible. A temperature sensor, such as a thermistor 108, could be bonded to the exterior sidewall of tube 106.

The different sensors described above all serve to provide the alarm processor 62 with the temperature of the injected fluid near the entry point of the needle into the patient limb 44. The system 42 in FIG. 2 thus provides continuous data regarding tissue temperature and fluid temperature to the alarm processor 62 and thus allows the-alarm processor 62 to adjust the alarm thresholds in real time.

The extravasation detection algorithm run by the processor 64 of the alarm processor 62 adjusts at least one and preferably two alarm thresholds depending on the fluid and tissue temperatures. If the difference between fluid and tissue temperature is large the thresholds should be large. Otherwise the filling of a normal vein with cold fluid could falsely trigger the alarm. When the temperature difference between fluid and tissue temperature is small, then the thresholds must be at their minimum to provide the protection required. The subcutaneous tissue temperature taken from antenna 58 is stored in memory 66 and is constantly compared with updated thresholds by the alarm processor 62. If the tissue temperature or a function determined by the tissue temperature exceeds a calculated threshold (indicating an extravasation or infiltration) at a given time the processor 62 sends a signal via the control signal output 74 to the injector head 54 to stop the injection. The signal output 74 may also activate user interface 56 to alert the user that an extravasation or infiltration has occurred. Typically threshold values are updated every 0.1 sec. during a 50 second injection using a flow rate of 3 ml/sec. Obviously different flow rates will determine different update rates of the threshold values.

The threshold values may be asymmetric. If it is known that the fluid is warmer than the tissue then the threshold for a temperature increase could be less than for a temperature decrease or a temperature decrease could be ignored altogether. Additionally, the algorithm provides a threshold minimum ($R_{min\_T}$) below which the system cannot go without having an unacceptable rate of false positives. The alarm processor 62 then alerts the user that the temperature difference between tissue and fluid temperatures is too low for reliable extravasation detection.

An additional feature of the present invention is to allow an operator to input data relating to the patient which may affect the threshold values chosen by the alarm processor 62. These data are typically stored in the memory 66 of the alarm processor 62 for later use by the extravasation detection algorithm. One method of modifying the threshold values is to allow the user to select among several discrete levels of sensitivity. The operator can base this judgment on factors which influence the likelihood of extravasation, such as patient age, weakened veins, general health depth of veins size or diameter of veins obesity type of the vascular entry device used the difficulty inserting the vascular entry device into the vein, and confidence that the needle is properly positioned. Other specific procedural physiological or anatomical information may be considered.

The above factors (hereinafter sometimes referred to as "Patient Parameters") which may influence the threshold values are determined by data gathered through clinical experience. The flexibility of selecting these factors employs the operator's judgment in balancing the likelihood of false positives against the likelihood of false negatives (where an extravasation occurs but the alarm does not occur).

Figure 9A:
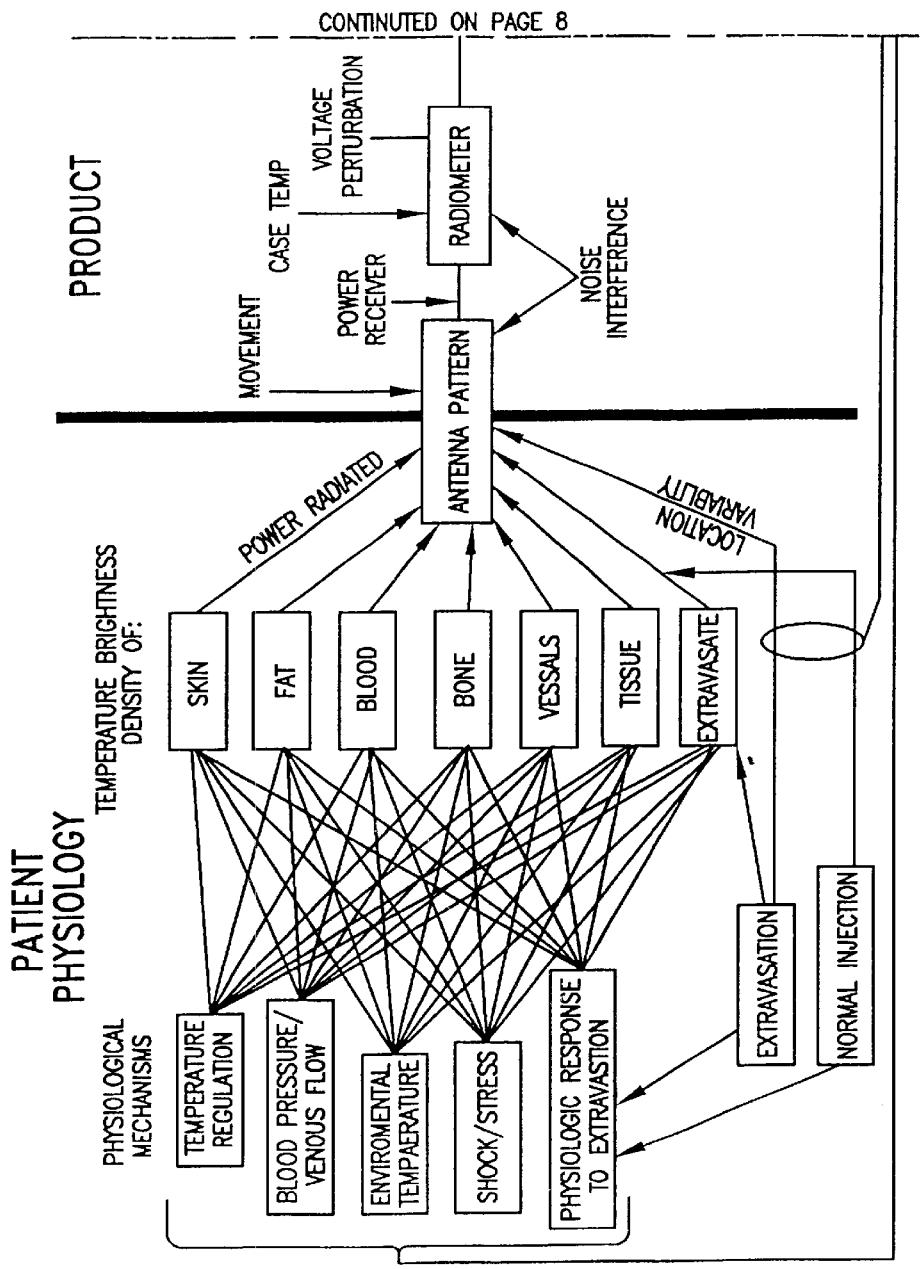
FIG. 9 is a chart showing the factors taken into consideration in a neural net analysis of specific patient factors according to the invention.
Figure 9B:
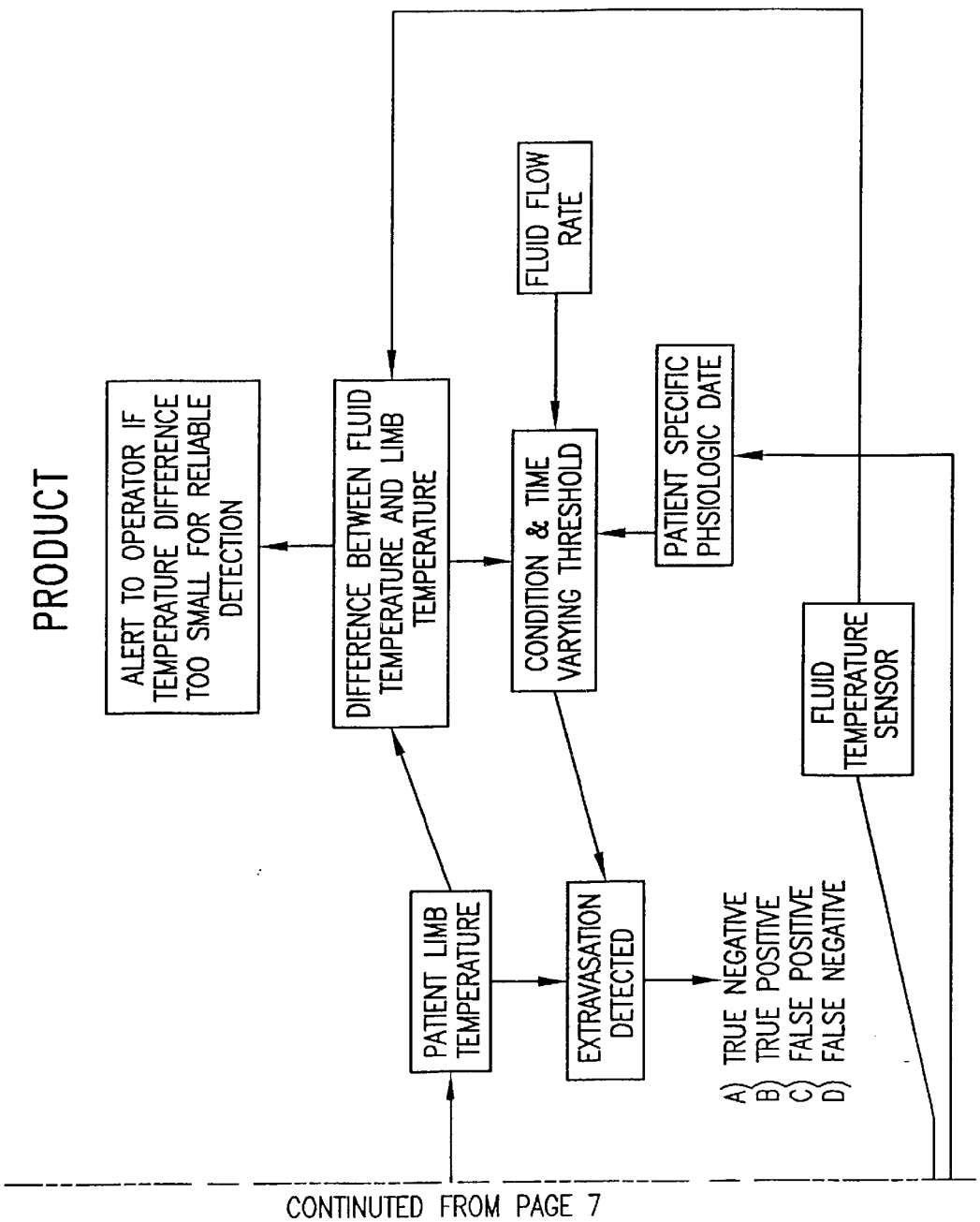

After enough data are collected from clinical experience a modified threshold selection algorithm could be incorporated in the alarm processor 62. The operator can answer questions about the patient through a user interface. An algorithm either one that is deterministic or that has the ability to learn over many injections then modifies the standard thresholds using the patient specific parameters. FIG. 9 is a chart of the factors which may be processed by a neural network to influence the threshold values.

Figure 10A:
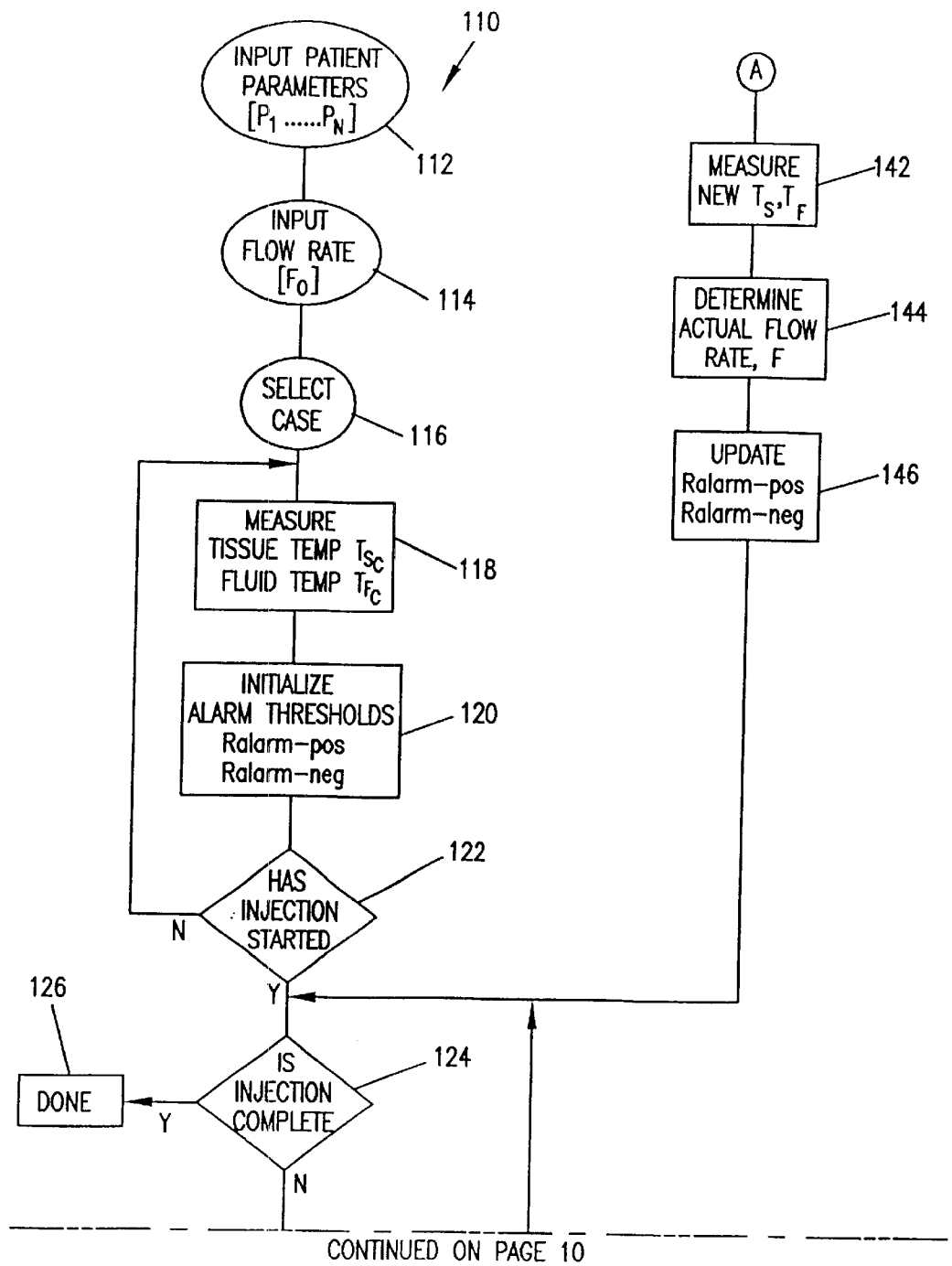
FIG. 10 is a flow diagram of an algorithm according to the present invention used to determine alarm threshold levels and to detect extravasations.
Figure 10B:
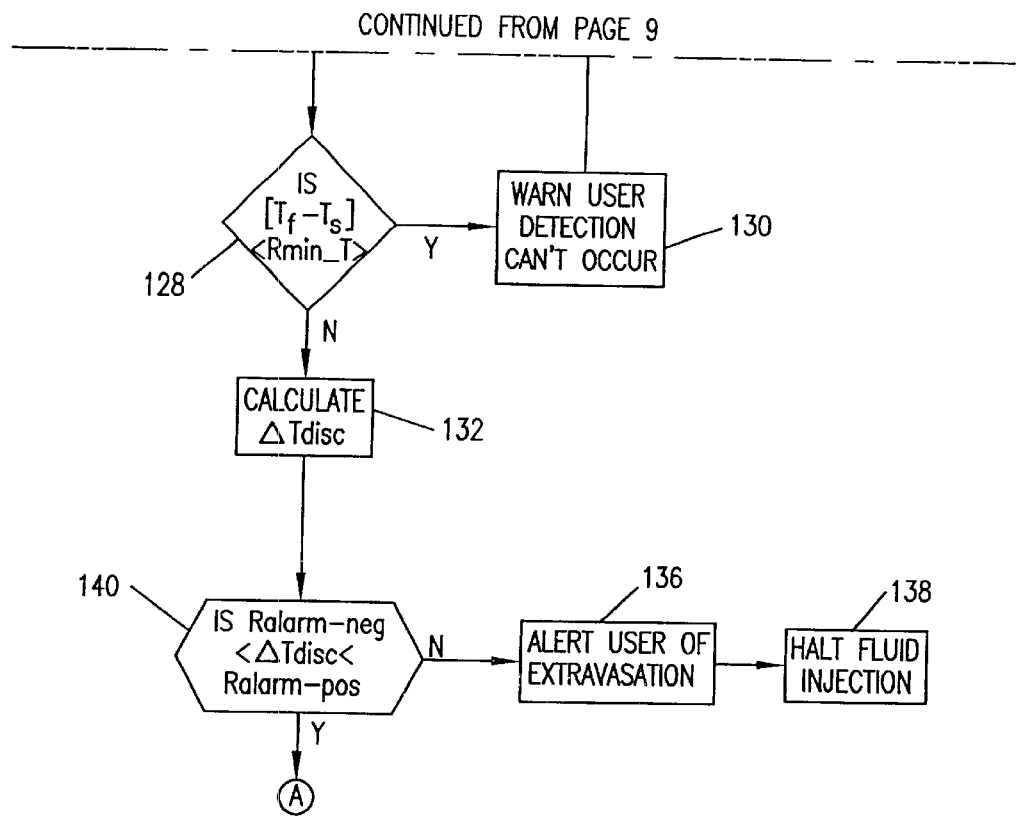

FIG. 10 is a flow diagram indicated generally at 110 of the algorithm used by the alarm processor 62 to determine threshold levels and to activate the alarm signal to the injector 54. As will be appreciated by those skilled in the art, other algorithms may be used.

The flow diagram 110 begins with step 112 at which Patient Parameters $P_{1\ldots n}$ are input. As explained above these may be factors such as general health depth of veins, size or diameter of veins, or obesity. The Patient Parameters $P_{1\ldots n}$ may be entered into the processor 64 of the alarm processor 62 (see FIG. 2) by the operator. In step 114, the programmed flow rate, $F_o$, is input by the operator and stored in memory 66 for use. The programmed flow rate is an initial estimate used for the delivered fluid. In step 116, the processor 64 or the user selects one of at least three cases (simple temperature difference, time delayed temperature difference, or at least one other algorithm fitting within the general case of a temperature discrimination function) which in turn determines the proper calculations to use to calculate initial and updated threshold temperature values. In step 118, the initial fluid temperature, $T_{f_o}$, and initial tissue temperature. $T_{s_o}$, are then taken from fluid temperature input 70 and tissue temperature input 68 respectively. These values are stored in memory 66 for use by the algorithm as will be described below. In step 120 the initial positive and negative alarm threshold values $R_{alarm\_pos}$ and $R_{alarm\_neg}$, are established as functions of patient parameters $P_{1\ldots n}$, injection flow rate F, and the initial tissue temperature and fluid temperatures. The positive and negative threshold values allow for asymmetric threshold settings which account for asymmetrical physiological responses. The positive and negative threshold alarms may be established according to the fictions described below in conjunction with step 146.

In step 122, the injector head input 72 is checked to determine whether the fluid injection has commenced. If the fluid injection has not commenced the algorithm loops back to step 118 and measures tissue and fluid temperature again to perform step 120 to update the initial alarm threshold values. If the fluid injection has commenced, step 124 is performed to check injector head input 72 to determine whether the fluid injection has been completed. If the fluid injection is complete the algorithm branches to step 126 and ends. If the fluid injection has not been completed the absolute value of the difference between the fluid and tissue temperature is taken and compared with the minimal difference threshold, $R_{min\_T}$ in step 128. The minimal difference threshold $R_{min\_T}$ is a predetermined constant or may be a function of some of the patient parameters. For example for a typical CT injection, the minimal difference threshold $R_{min\_T}$ has a value of 1° C. If the absolute value of the difference of the fluid and tissue temperatures is less than the minimal difference threshold $R_{min\_T}$, the user is alerted that detection of extravasations cannot occur in step 130. An alternative method may be to set a range of acceptable differences in fluid and tissue temperature for asymmetric operation thereby comparing the value of the difference between tissue aid fluid temperatures with a negative and positive threshold value.

In step 132, assuming that the absolute difference of the fluid and tissue temperature is above the minimal threshold a temperature discrimination function $\_T_{disc}$, is determined based on the case selected for the algorithm. In the case of simple temperature difference, $_{13}T_{disc}$ is determined as follows:

$$\_T_{disc}=T_s-T_{s_o}$$

where $T_s$ is the current tissue temperature and $T_{s_o}$ is the initial tissue temperature at the beginning of the fluid injection. The temperature discrimination function is thus the simple temperature difference between the current tissue temperature and the initial tissue temperature at the beginning of the injection.

In the case of time delayed temperature difference, $\_T_{disc}$ is determined as follows:

$$\_T_{dis}=T_s-T_{s_{t-t}}$$

where the temperature discrimination function reflects the temperature difference between the most recent tissue temperature and some other tissue temperature measurement taken at time t-t which is for a predetermined interval prior to the current time. In this last instance the processor 64 (see FIG. 2) causes a periodic series of tissue temperatures to be stored in memory 66 from which they are sequentially retrieved at each time that the temperature discrimination function is recalculated.

In the general case of the temperature discrimination function, $_{13}T_{disc}$ is determined as a function of tissue temperatures at different time increments:

$$\_T_{disc}=fyl\ (T_{s_i}), i=0,1,2\ldots n$$

Any number of temperature discrimination functions fit within the general case, including first and higher derivatives of the tissue temperature with respect to time.

The $\_T_{disc}$ calculated in step 132 is compared with the initial positive and negative alarm threshold values, $R_{alarm\_pos}$ and $R_{alarm\_neg}$, in step 140. If $\_T_{disc}$ exceeds the positive alarm threshold $R_{alarm\_pos}$ or is below the negative alarm threshold, $R_{alarm\_neg}$, step 136 is implemented such that an alarm signal is generated to warn the user that an extravasation or infiltration has occurred. The alarm processor 62 can respond by halting fluid flow from the fluid injector 54 as in step 138. The alarm processor 62 may also place the injection in a hold state so the operator may check the patient. An option may be given to restart the injection or to override the alarm.

If $\_T_{disc}$ is within the positive and negative thresholds in step 140, new tissue and fluid temperature values are determined from antenna 58 and temperature sensor 76 in step 142 and stored in memory 66. The actual flow rate, F, is also ascertained from the fluid injector input 72 in step 144 and stored in memory 66.

The alarm thresholds $R_{alarm\_pos}$ and $R_{alarm\_neg}$ are then updated in step 146 according to the case selected in step 116. In the cases of a simple temperature difference and time delayed temperature difference, the alarm thresholds are updated as follows:

$$R_{alarm\_pos} = \text{Max}[C_1, C_2 \cdot (T_s - T_f)]$$

$$R_{alarm\_neg} = \text{Min}[C_3, C_4 \cdot (T_s - T_f)]$$

Constants $C_{1-4}$ are determined by clinical data. For example they may be determined as a function of flow rate and vein diameter.

In the general case of the temperature discrimination function the alarm thresholds may be stated as follows.

$$R_{alarm\_pos} = f_3(P_1 \ldots n, F, T_{s_i}, T_{f_i})$$

$$R_{alarm\_neg} = f_4(P_1 \ldots n, F, T_{s_i}, T_{f_i})$$

The alarm thresholds are calculated as a function of patient parameters $P_1 \ldots n$ injection flow rate, F, and the tissue temperature and fluid temperatures taken and stored for selected times. Many different specific algorithms may be used which are included in the above general case, including those which use first and higher derivatives of the tissue and/or fluid temperatures with respect to time.

After updating the alarm thresholds and tissue and fluid temperatures, the checks are performed repeatedly until the end of the fluid injection is determined at step 124. This adaptive algorithm 110 allows the thresholds to be adjusted for changing temperatures to allow for more reliable detection. If desired several different calculation techniques may be considered by the algorithm. For example different alarm thresholds and temperature discrimination functions maybe compared by the alarm processor 62 with each other for greater reliability.

Figure 12:
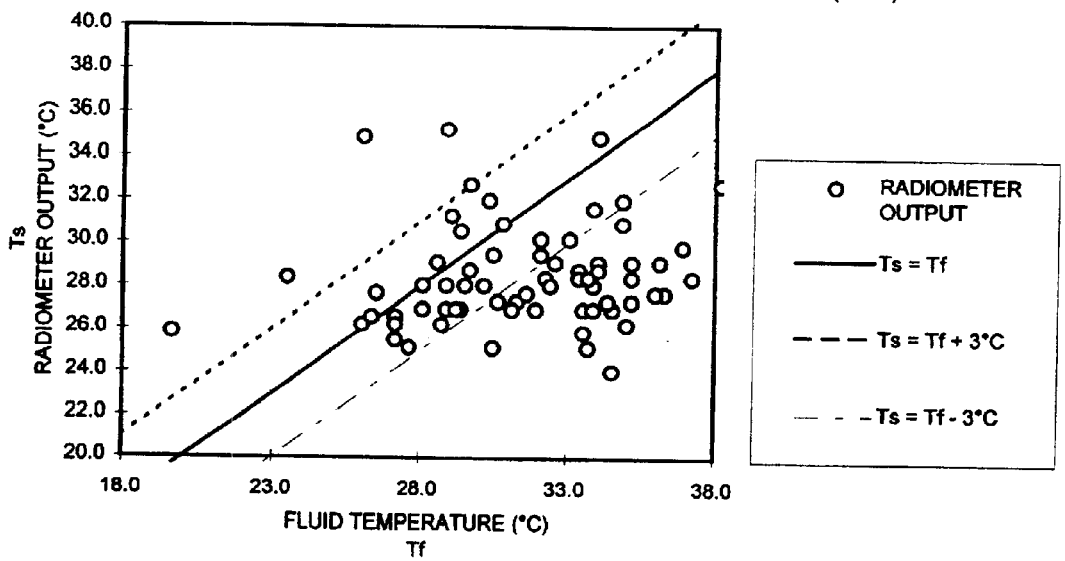
FIG. 12 is a graph illustrating the radiometer output versus fluid temperature twenty seconds after injection.
Figure 11:
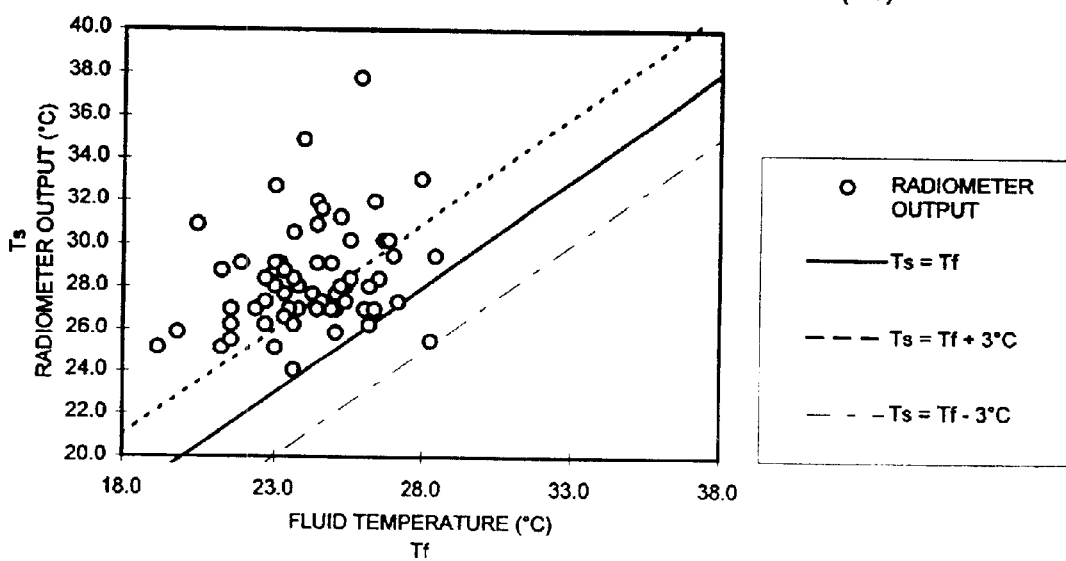
FIG. 11 is a graph illustrating the radiometer output versus fluid temperature at the start of injection.

FIG. 11 is a graph of the tissue temperature and the fluid temperature at the beginning of a fluid injection procedure. The tissue temperature is measured by the radiometer 60 based upon calibration using a water phantom while the fluid temperature is measured with the clip-on temperature sensor 76. These data illustrate that the tissue temperature and the fluid temperature may be very close in clinical situations. As may be seen a fraction of the measurements lies within an initial minimum fluid/tissue difference of 1 degree Celsius. FIG. 12 is a graph of tissue temperature and fluid temperature 20 seconds after the beginning of fluid injection.

The relatively cold temperature of the fluid $T_f$ in FIG. 11 results from fluid residence prior to injection in the connector tube 48. The alarm thresholds $R_{alarm\_pos}$ and $R_{alarm\_neg}$ will vary as a function of the value of $T_s - T_f$. As the temperature difference increases the value of $\Delta T_{disc}$ necessary to trigger an alarm also increases.

As the fluid temperature warms up reflecting the fact that the fluid being injected has only been in the relatively cold connector tube 48 for a short time period $T_s - T_f$ will decrease and subsequently increase and $R_{alarm\_pos}$ and $R_{alarm\_neg}$ will also decrease and subsequently increase. FIGS. 11 and 12 demonstrate the technical advantage in adjusting the alarm thresholds to take fluid temperature changes into account.

Figure 14:
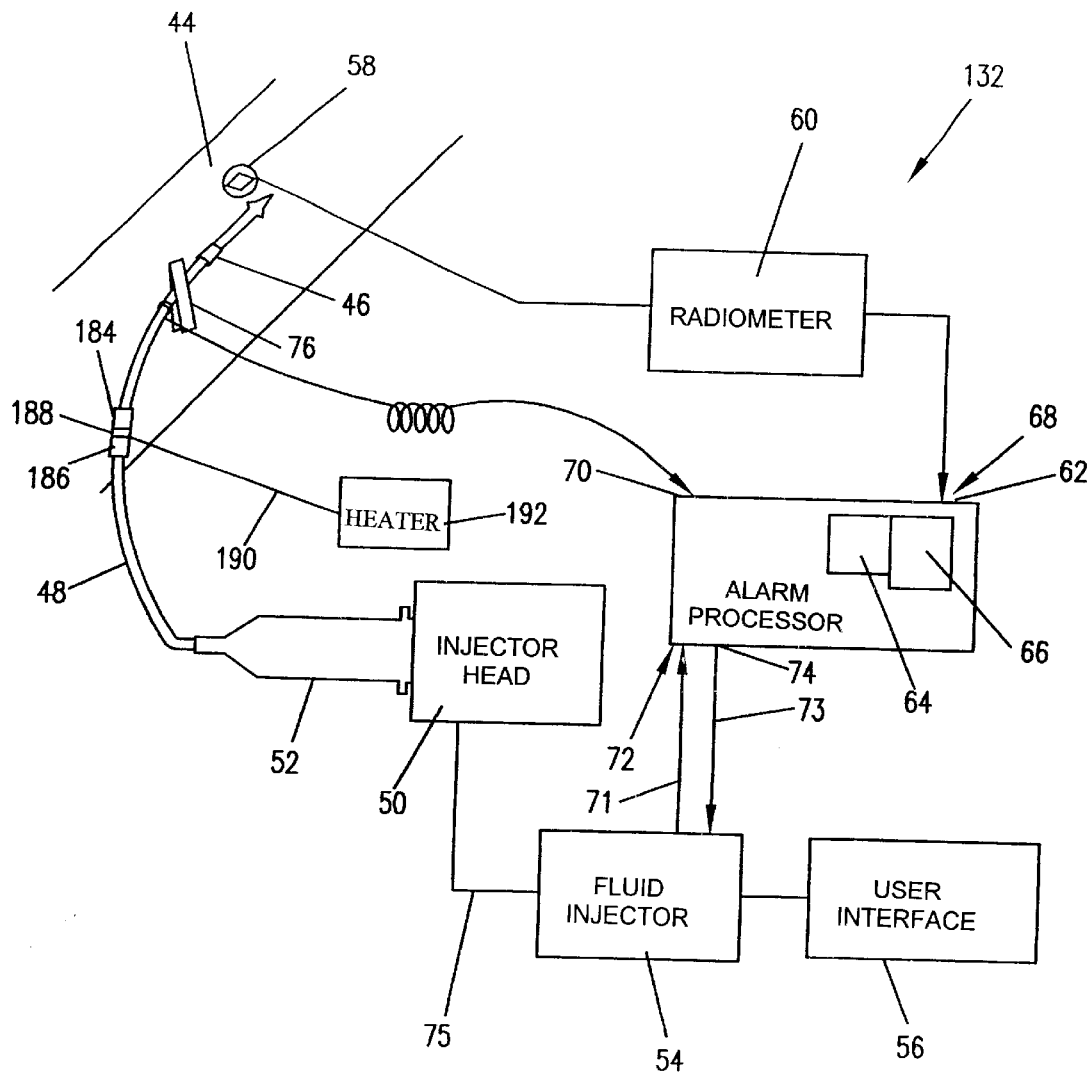
FIG. 14 is a schematic block diagram of an embodiment of the present invention in which a heating/cooling element is attached to the connector between a needle and a tube.

FIG. 14 is a block diagram of a fourth embodiment of the present invention indicated generally at 182. Like elements have numbers identical to their counterparts in FIG. 2. FIG. 14 shows a configuration where a heating/cooling element 184 is attached to the connector tubing 48. The heating cooling element 184 has a small mass of thermally conductive material 186 which is embedded within a connector 188 between ends of the tubing 48. The mass 186 allows quick heat transmission to or from the fluid. The mass 186 may be connected to a heater 192 via a line 190 in order to be energized to heat the fluid. This arrangement allows heating or cooling to be expedited, similar in concept to the rapid response of the fluid temperature sensor in FIGS. 5–7.

The fluid may also be cooled by passing a portion of the connector tubing 48 through a thermally conductive material with a large thermal mass such as an aluminum block at room temperature (not shown). Heat is dissipated from the fluid since room temperature is typically less than tissue temperature in most environments. This arrangement allows some cooling of the fluid before it is injected so that a minimum temperature difference between fluid and tissue temperature is achieved. The fluid may also be heated by warming the block to some elevated constant temperature. No measurement of fluid temperature is needed if the thermal conductivity and thermal mass are chosen large enough to maintain a relatively consistent fluid temperature. In another approach, a thermoelectric or other heating or cooling device is attached to a block of thermally conductive material with sizable thermal mass so that the fluid gains or loses heat to or from the block.

Figure 15:
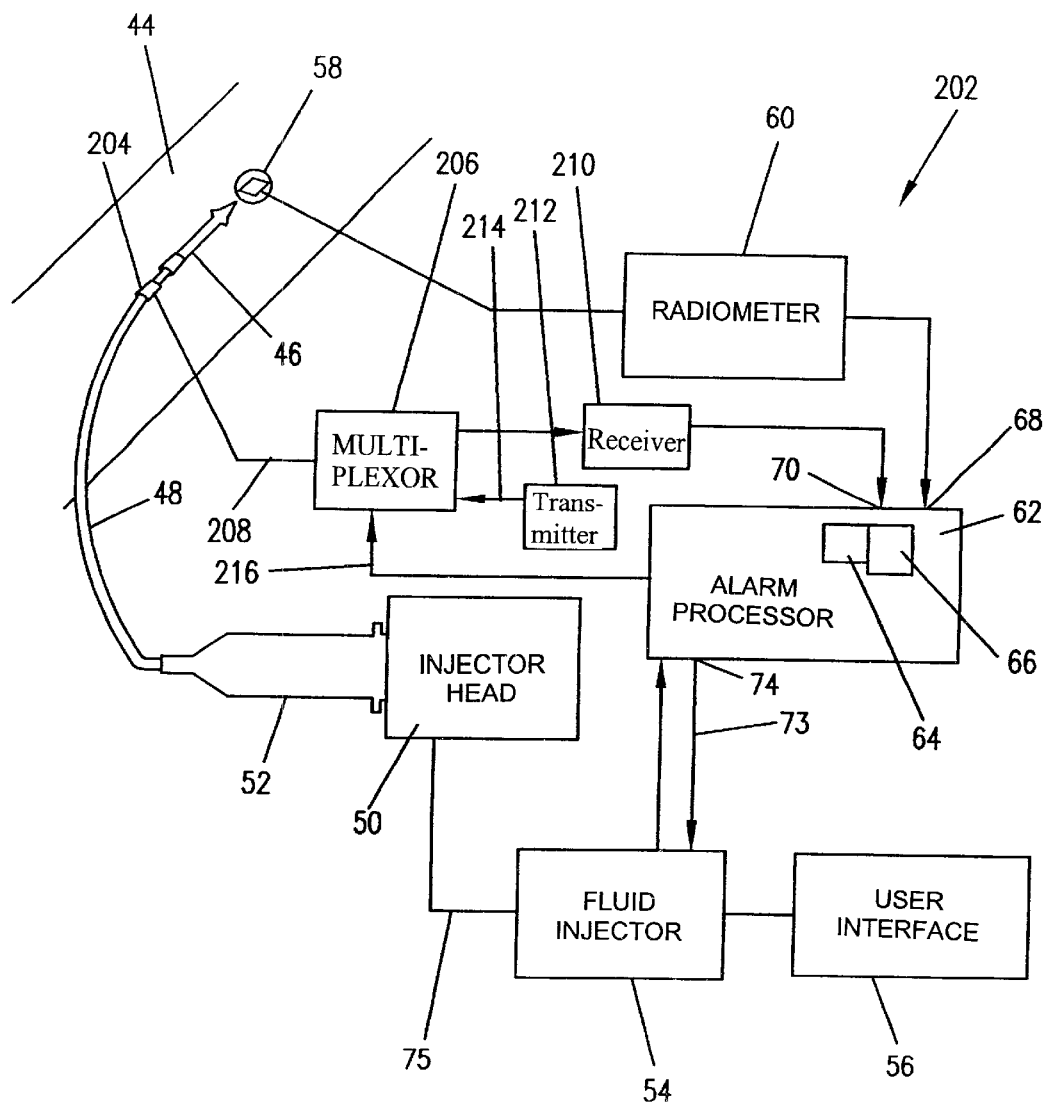
FIG. 15 is a schematic diagram of an embodiment of the present invention in which a microwave antenna is used for sensing fluid temperature and for heating the injected fluid.

FIG. 15 is a block diagram of a fifth embodiment of the present invention indicated generally at 202. Like elements have numbers identical to their counterparts in FIG. 2. FIG. 15 shows a configuration where a microwave antenna 204 is attached to tubing 48. The microwave antenna 204 is coupled to a multiplexor 206 via a line 208. The multiplexor 206 allows the microwave antenna 204 to be connected to either a radiometer receiver 210 which is coupled to processor 62 via input 70 or a microwave transmitter 212 via line 214. The multiplexor 206 is activated and controlled by the alarm processor 62 via selection line 216.

The microwave antenna 204 is used to measure fluid temperature when multiplexor 206 is selected to choose connection of the radiometer receiver 210 via line 208. In this selection mode the antenna 204 senses fluid temperature similar to antenna 58. If the fluid temperature needs to be raised to allow sufficient temperature difference for extravasation detection, the multiplexor 206 is selected to a second mode via line 216. The microwave antenna 204 then transmits energy from microwave transmitter 212 which causes antenna 204 to emit energy to the fluid and heat the fluid. The radiometer receiver 210 is isolated from the transmitter output signal when the transmitter 212 is active. Of course other sensors which may be used as heating elements and sensors such as thermistors and metal foil heating elements where the element can dissipate energy as heat and the electrical resistance or some other property of the same element changes with temperature to allow for temperature sensing may be substituted for the microwave -antenna 204. Additionally, separate control lines to sensors and heating elements may be used instead of the multiplexor arrangement.

Figure 16A:
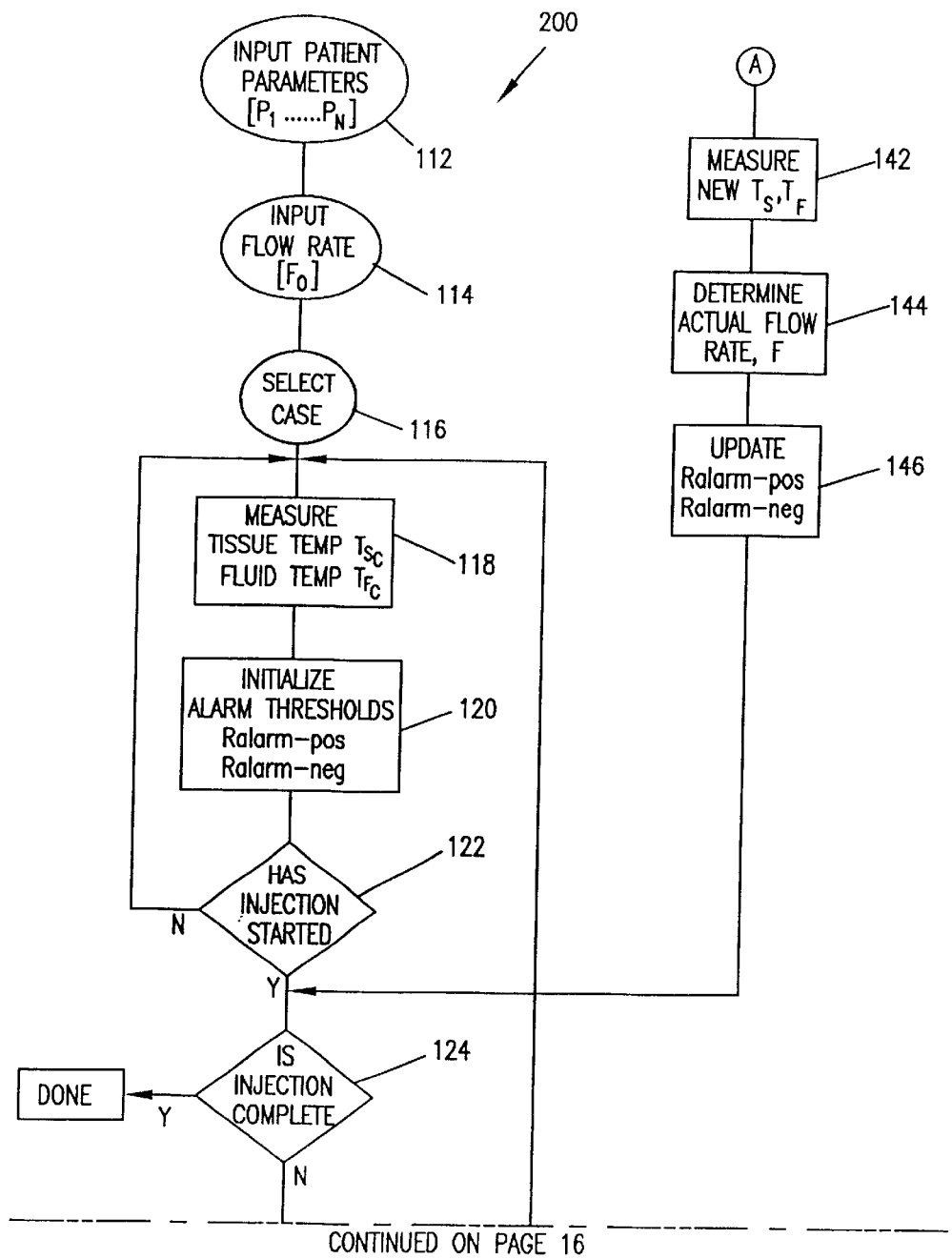
FIG. 16 is a flow diagram of a modified algorithm according to the present invention used to determine alarm threshold levels and to detect extravasations.
Figure 16B:
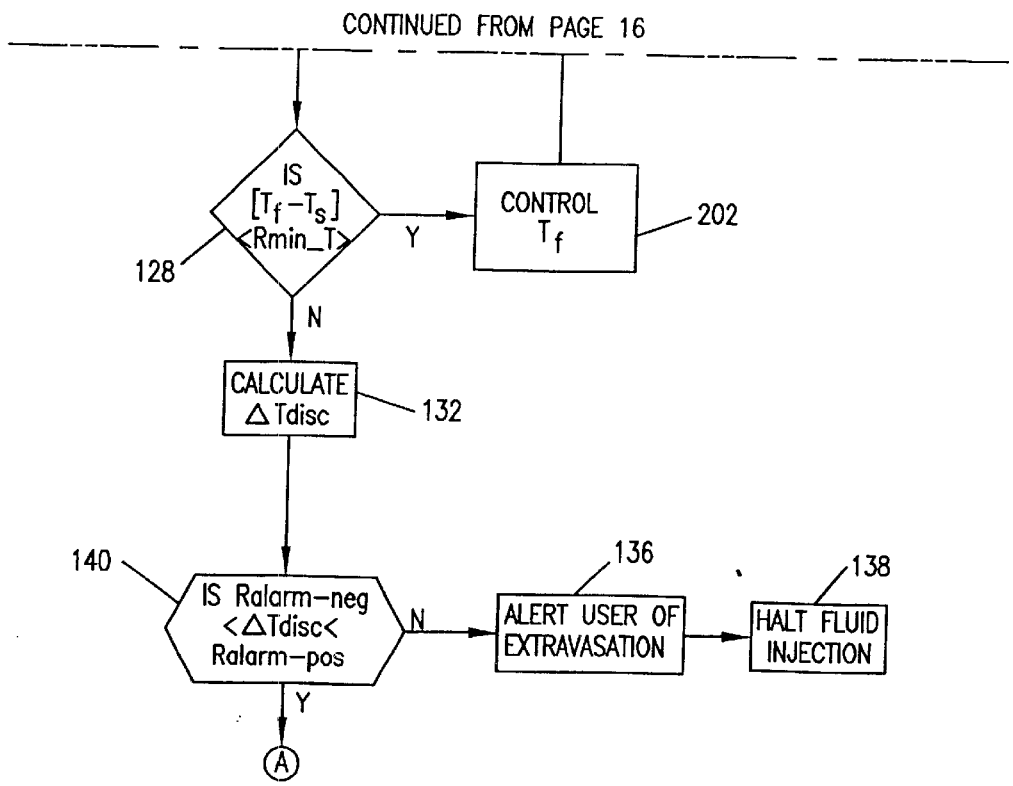

The above described fourth and fifth alternate embodiments allows detection of extravasations when the difference in fluid and tissue temperatures is not sufficiently large. The algorithm described above need only be modified as shown in the flow diagram in FIG. 16. FIG. 16 shows a modified algorithm 200 which is similar to the algorithm in FIG. 10. Like numbers represent identical steps to the flow diagram in FIG. 10. As in the algorithm in FIG. 10, initial patient parameters, flow rate and case are selected or input in steps 112, 114, and 116. After measuring the initial tissue and fluid temperature in step 118 and initializing the alarm thresholds in step 120, whether the injection has been started or is complete is determined in steps 122 and 124. The difference between tissue and fluid temperature is then compared with the minimal difference threshold in step 128. Like the previous algorithm, if the difference of the fluid and tissue temperature is greater than the minimal difference threshold, the algorithm proceeds to check for extravasations and update threshold values. If the difference is less than the minimal difference threshold the fluid temperature is controlled in step 202 in order to increase the difference between fluid and tissue temperature. Once the fluid temperature has been changed sufficiently, the algorithm loops back to step 118 and measures tissue and fluid temperatures.

Thus, the fluid temperature and the tissue temperature are measured and one or both may be controlled so that a minimum temperature difference $R_{min\_T}$, of several degrees Celsius needed for reliable extravasation detection is established between the fluid and tissue temperature. This method improves detection reliability since the condition where fluid temperature and tissue temperature are similar is precluded by temperature control of the delivered fluid temperature, or control of tissue temperature or control of both temperatures. The temperature control greatly reduces the occurrences where the operator is warned that reliable detection cannot take place because a minimum temperature difference does not exist. This method is desirable since similar temperatures are frequent during normal clinical use as media for CT injections and other injections is often preheated to approximately body temperature for patient comfort before the fluid is injected.

In order to achieve a minimum temperature difference between the fluid and tissue temperatures, both temperatures are measured and the fluid or tissue may either be heated or cooled to provide a minimum difference between the two. After fluid or tissue temperature is corrected to obtain a minimal threshold difference between fluid and tissue temperature, the same extravasation detection algorithm previously described based on fluid and tissue temperature measurements may be used in conjunction with this method. If the fluid temperature is controlled well enough at the point close to the patient's limb, other algorithms with fixed thresholds depending only upon flow rate may be used. Measurement or control of the fluid temperature at the point of injection overcomes the problems of false alarms. The steps of the previously described algorithm which determine and warn of an insufficient fluid and temperature difference may remain as a check on the proper operation of the temperature control portion of the device.

Cooling is preferable since the latitude for temperature increase of human body tissue and injected fluid is limited to a few degrees Celsius above normal core body temperature (approximately 37 degrees Celsius) otherwise tissue damage may occur. Fluid or tissue near the injection site may easily be cooled by the few degrees Celsius in temperature needed to ensure the minimum temperature difference condition exists for detection of extravasation. In most cases it should only be necessary to heat or cool the fluid to several degrees Celsius below or above tissue temperature for reliable detection of extravasation to take place.

Controlling fluid temperature is preferable to controlling tissue temperature since tissue thermal mass and conductivity may vary from patient to patient depending on limb size, anatomy, tissue content, and circulation influences. Fluid temperature may be controlled at the syringe or as it is delivered through the connector tubing. At the connector tube fluid may be cooled or heated through the use of a thermoelectric or other cooling device in line or around the tubing as shown in FIG. 14. As with the fluid temperature sensor it is advantageous to place the heating or cooling element near the injection site and fluid temperature sensor to minimize temperature measurement errors of the estimated fluid temperature at the injection site and to minimize control lag errors from heat dissipation at the connector tubing to the ambient environment.

Figure 13:
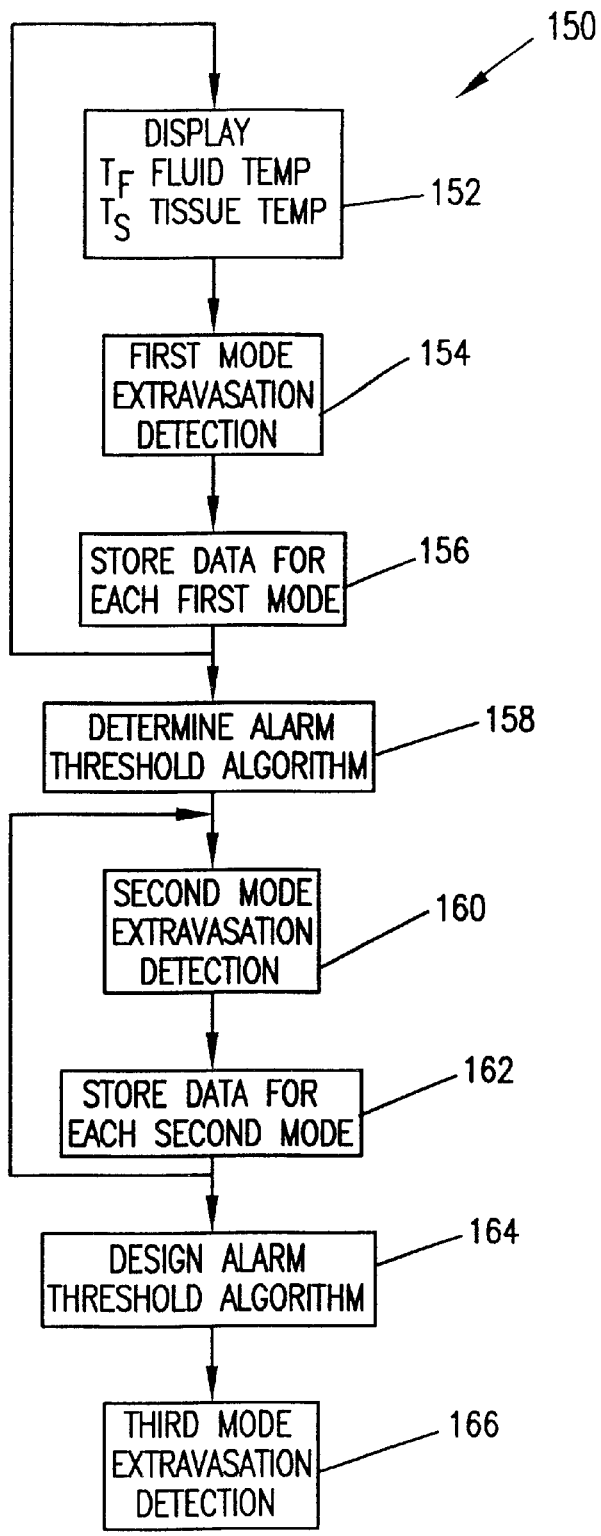
FIG. 13 is a flow diagram of the various modes of operation according to the present invention.

Another feature of the present invention is using the alarm processor 62 in one operating mode, and then modifying it to operate in other modes. FIG. 13 shows a block diagram 150 of an algorithm for modifying the operating mode of the alarm processor 62. A considerable amount of human clinical data is needed to precisely determine the alarm threshold settings and algorithm for modification. Initially the system displays the fluid and tissue temperatures ($T_f$, $T_s$) for the operator in step 152. This may be done through a user interface on alarm processor 62 (not shown). The operator can look at these data and query the patient about pain if the traces seem abnormal. Extravasation detection takes place in an initial mode in step 154 using threshold values based solely on the fluid and tissue temperatures. In the step 156 the alarm processor 62 stores significant data from each injection in the first mode 154 for subsequent retrieval and processing. Alternatively an independent storage device such as a database in a computer may be used to store the significant data.

After enough data are collected from clinical sites an alarm threshold algorithm can be determined and then installed in the memory 66 of processor 62 as in step 158. A second mode of extravasation detection 160 could use a user-selectable threshold scale mentioned above but not use patient-specific data to modify the thresholds.

While operating in the second mode 160 patient data would be collected and stored as in step 162. Algorithms are then designed in step 164 to allow operation in a third mode of extravasation detection 166 where patient specific data influence the thresholds. The system could then be changed to operate in the third mode 166 left in the second mode 160, or even in the first mode 154, depending upon operator preference.

The present invention is not limited to CT applications. For example, the present invention may be used to detect extravasations in any fluid injection application such as IV injections. Such a system is not limited to electrically driven fluid delivery pumps but could be used with hand driven, mechanical, or gravity driven fluid injectors (such as an IV drip bag). Additionally, one skilled in the art will appreciate that dedicated electronic circuits may replace part or all of the algorithm used by the alarm processor circuit to perform the various detection and alarm functions.

Although the present invention has been described in terms of preferred embodiments, the present description is given by way of example and is not intended to be limiting to the scope of the invention described and claimed herein.

What is claimed is:

1. An apparatus for detecting extravasations in tissue injected with fluid, the apparatus comprising:

a fluid temperature sensor for sensing the temperature of fluid present in a fluid path element which transmits fluid to a patient and generating a fluid temperature signal in response thereto;

a tissue temperature sensor for sensing the temperature of tissue proximate to the site of injection and generating a tissue temperature signal in response thereto; and a processor adaptable to periodically receive said tissue temperature signal and said fluid temperature signal, said processor having an alarm circuit for declaring the occurrence of an extravasation and a threshold calculation circuit for periodically calculating at least one threshold value as a function of said tissue temperature signal and said fluid temperature signal, said processor activating said alarm circuit as a function of said tissue temperature signal, said fluid temperature signal and said at least one threshold value during a fluid injection.

2. The apparatus of claim 1 wherein said fluid temperature sensor is associated with a connector tube.

3. The apparatus of claim 1 wherein said fluid temperature sensor is associated with a syringe.

4. The apparatus of claim 1 wherein said fluid temperature sensor is associated with a catheter.

5. The apparatus of claim 1 wherein said fluid temperature sensor comprises a microwave antenna and a radiometer coupled to the microwave antenna.

6. The apparatus of claim 1 wherein said tissue temperature sensor comprises a microwave antenna and a radiometer coupled to the microwave antenna.

7. The apparatus of claim 1 wherein said processor further comprises:
- a circuit for deriving at least first and second tissue temperatures from said tissue temperature signal at different times;
- a circuit for deriving a fluid temperature from said fluid temperature signal;
- a memory for storing said first and second tissue temperatures and said fluid temperature;
- a temperature discrimination function circuit for calculating a temperature discrimination function as a function of said first and second tissue temperatures; and
- a comparison circuit for comparing said temperature discrimination function with said at least one threshold, said comparison circuit activating said alarm circuit to declare an extravasation when the value of said temperature discrimination function exceeds said at least one threshold.

8. The apparatus of claim 7 wherein said threshold calculation circuit calculates a first, positive threshold as a function of said second tissue temperature and said fluid temperature, said threshold calculation circuit further calculating a second negative threshold as a function of said second tissue temperature and said fluid temperature, said comparison circuit activating said alarm circuit when either the value of said temperature discrimination function exceeds said first threshold or when the value of said temperature discrimination function is less than said second negative threshold.

9. The apparatus of claim 7 wherein said temperature discrimination function circuit periodically calculates the temperature discrimination function as the difference between said fluid tissue temperature and each of a plurality of sequentially-determined second tissue temperatures.

10. The apparatus of claim 7 wherein said first tissue temperature is a tissue temperature at the beginning of the fluid injection and said second tissue temperature is a current tissue temperature.

11. The apparatus of claim 1 further comprising means for entering and storing at least one patient parameter said threshold calculation circuit calculating said at least one threshold value as a function of said at least one patient parameter.

12. The apparatus of claim 11 wherein said at least one patient parameter is selected from the group consisting of age, vein condition, vein size, vein depth, health of the patient, obesity, type of vascular entry device being employed, vascular insertion difficulty and needle positioning confidence.

13. The apparatus of claim 11, further comprising means for receiving a fluid flow rate for the fluid to be injected said threshold calculation circuit calculating said at least one threshold value as a function of said fluid flow rate.

14. The apparatus of claim 1 wherein said threshold circuit is further operable to take initial tissue and fluid temperatures and calculate a threshold value based on said initial tissue and fluid temperatures, and further wherein said processor further comprises a discrimination circuit operable to calculate a temperature discrimination function based on said initial tissue temperature and a current tissue temperature said discrimination circuit operable to activate said alarm circuit if said temperature discrimination function exceeds said initial threshold value.

15. The apparatus of claim 14 wherein said threshold circuit further comprises a circuit for determining updated fluid and tissue temperatures and a circuit for calculating an updated threshold value and further wherein said discrimination circuit further comprises a circuit for calculating an updated temperature discrimination function and a circuit for activating said alarm circuit if said updated temperature discrimination function exceeds said updated threshold value.

16. The apparatus of claim 1 wherein said processor further comprises a warning circuit which compares the difference of said fluid temperature and said tissue temperature to a minimal difference threshold to warn that no extravasation detection is possible.

17. An apparatus for detecting extravasations in tissue injected with fluid, the apparatus comprising:
- a fluid temperature sensor for sensing the temperature of fluid proximate to the site of injection and generating a fluid temperature signal in response thereto;
- a tissue temperature sensor for sensing the temperature of tissue proximate to the site of injection and generating a tissue temperature signal in response thereto; and
- a processor adaptable to periodically receive said tissue temperature signal and said fluid temperature signal said processor having an alarm circuit for declaring the occurrence of an extravasation and a threshold calculation circuit for periodically calculating at least one threshold value as a function of said tissue temperature signal and said fluid temperature signal said processor activating said alarm circuit as a function of said tissue temperature signal said fluid temperature signal, and said at least one threshold value during a fluid injection.

18. A fluid temperature sensor comprising:
- a temperature transducer operably associated with an extravasation detector; and
- a thermally conductive insert coupled to said temperature transducer and operably associated with a fluid path element for delivering fluid to a patient during a fluid injection said insert adapted to extend through the fluid path element into contact with the fluid therein to provide a temperature conductive path between the fluid and said temperature transducer.

19. The fluid temperature sensor of claim 18 wherein said transducer comprises a thermistor.

20. The fluid temperature sensor of claim 18 wherein said transducer comprises a thermocouple.

21. A method of detecting extravasations in tissue injected with a fluid, comprising:
- periodically sensing the temperature of the fluid present in a fluid path element transmitting fluid to a patient;
- generating a fluid temperature signal in response to the periodic sensing of fluid temperature;
- periodically sensing the temperature of tissue proximate to the site of injection;
- generating a tissue temperature signal in response to the periodic sensing of tissue temperature;
- receiving the fluid temperature signal and the tissue temperature signal;

storing a fluid temperature and a tissue temperature derived from the received signals; and declaring the occurrence of an extravasation as a function of said tissue temperature signal and said fluid temperature signal during a fluid injection.

22. The method of claim 21 further comprising:

determining initial tissue and fluid temperatures;

calculating at least one initial threshold value as a function of the initial tissue and fluid temperatures;

calculating a temperature discrimination function based on the initial tissue temperature; and activating an alarm if the temperature discrimination function exceeds the at least one initial threshold value.

23. The method of claim 22 further comprising:

determining updated fluid and tissue temperatures;

calculating at least one updated threshold value as a function of the updated fluid and tissue temperatures;

calculating an updated temperature discrimination function; and activating the alarm if the updated temperature discrimination function exceeds the at least one updated threshold value.

24. The method of claim 22, further comprising:

comparing the difference between the fluid temperature and the tissue temperature to a minimal difference threshold; and warning that no extravasation detection is possible if the minimal difference threshold exceeds the difference.

25. A method of detecting extravasations in tissue injected with a fluid, the method comprising:

measuring a tissue temperature;

measuring a fluid temperature;

controlling the fluid temperature so the difference between the tissue temperature and the fluid temperature is sufficient to permit extravasation detection; and declaring the occurrence of an extravasation as a function of the tissue temperature and the fluid temperature.

26. A fluid injection system comprising:

an injector operable to initiate and terminate fluid flow into a patient;

a fluid path element coupled to said fluid injector for transmitting fluid to the patient;

a fluid temperature sensor associated with said fluid path element said temperature sensor producing a fluid temperature signal representing the temperature of the fluid in said fluid path element;

a tissue temperature sensor for generating a tissue temperature signal as a function of the temperature of the tissue of the patient proximate to the injection site; and an alarm circuit coupled to said tissue temperature sensor and said fluid temperature sensor, said alarm circuit comprising a temperature discrimination function circuit operable to calculate a temperature discrimination function from the tissue temperature and a threshold circuit operable to compare at least a first threshold value with the temperature discrimination function, the threshold circuit calculating the at least a first threshold value at different time intervals during a fluid injection.

27. The fluid injection system of claim 26 wherein said tissue temperature sensor comprises an antenna disposed to receive microwave radiation from the tissue and a radiometer coupled to the antenna and operable to produce the tissue temperature signal.

28. The fluid injection system of claim 26 wherein said fluid temperature sensor comprises an antenna disposed to receive microwave radiation from the fluid and a radiometer coupled to the antenna for generating the fluid temperature signal.

29. The fluid injection system of claim 26 wherein said fluid path element comprises a syringe.

30. The fluid injection system of claim 26 wherein said fluid path element comprises a connector tube.

31. The fluid injection system of claim 26 wherein said fluid path element comprises a catheter.

32. The fluid injection system of claim 26 further comprising means for entering and storing at least one patient parameter and wherein the at least a first threshold value is calculated as a function of the at least one patient parameter.

33. The fluid injection system of claim 32 wherein the at least one patient parameter is selected from the group consisting of age, vein condition, vein size, vein depth, health of the patient, obesity, type of vascular entry device being employed, vascular insertion difficulty and needle positioning confidence.

34. An apparatus for detecting extravasations in tissue injected with a fluid, the apparatus comprising:

a tissue temperature sensor for sensing the temperature of the tissue proximate to the injection site and generating a tissue temperature signal in response thereto;

a fluid temperature controller for controlling the temperature of the fluid injected into the tissue; and a processor adaptable to receive the tissue temperature signal and a fluid temperature signal generated from the temperature of the fluid, said processor comprising an alarm circuit for declaring the occurrence of an extravasation as a function of the tissue temperature signal and the fluid temperature signal, said processor coupled to said fluid temperature controller to control the temperature of the fluid so that a minimum difference exists between the tissue temperature and the fluid temperature.

35. The apparatus of claim 34 wherein said fluid temperature controller comprises a temperature sensor for sensing fluid temperature and generating the fluid temperature signal.

36. An apparatus for detecting extravasations in tissue injected with fluid, the apparatus comprising:

a fluid temperature sensor for sensing the temperature of fluid present in a fluid path element which transmits fluid to a patient, and generating a fluid temperature signal in response thereto;

a tissue temperature sensor for sensing the temperature of tissue proximate to the site of injection and generating a tissue temperature signal in response thereto; and a processor adaptable to periodically receive said tissue temperature signal and said fluid temperature signal, said processor having an alarm circuit for declaring the occurrence of an extravasation and a threshold calculation circuit for periodically calculating at least one threshold value as a function of said tissue temperature signal, said fluid temperature signal and clinical experience based on one or more patients said processor activating said alarm circuit as a function of said tissue temperature signal said fluid temperature signal, and said at least one threshold value during a fluid injection.

37. The apparatus of claim 36, further comprising a user interface associated with said processor for allowing an operator to input patient parameters into the threshold calculation circuit, the patient parameters operable to modify the at least one threshold value.

* * * * *